(12) United States Patent
Rana et al.

(10) Patent No.: US 11,903,989 B2
(45) Date of Patent: *Feb. 20, 2024

(54) BOTANICAL MODULATOR OF METABOLIC DISORDERS

(71) Applicant: Innophos, LLC, Cranbury, NJ (US)

(72) Inventors: Jatinder Rana, Grand Rapids, MI (US); Kylie Mitchell, Pennington, NJ (US)

(73) Assignee: Innophos, LLC, Cranbury, NJ (US)

( * ) Notice: Subject to any disclaimer, the term of this patent is extended or adjusted under 35 U.S.C. 154(b) by 134 days.

This patent is subject to a terminal disclaimer.

(21) Appl. No.: 17/467,810

(22) Filed: Sep. 7, 2021

(65) Prior Publication Data

US 2021/0401917 A1 Dec. 30, 2021

Related U.S. Application Data

(62) Division of application No. 16/561,574, filed on Sep. 5, 2019.

(60) Provisional application No. 62/728,119, filed on Sep. 7, 2018.

(51) Int. Cl.
| | |
|---|---|
| *A61K 36/46* | (2006.01) |
| *A61K 36/45* | (2006.01) |
| *A61P 3/00* | (2006.01) |
| *A61K 31/353* | (2006.01) |

(52) U.S. Cl.
CPC ............ *A61K 36/45* (2013.01); *A61K 31/353* (2013.01); *A61P 3/00* (2018.01)

(58) Field of Classification Search
None
See application file for complete search history.

(56) References Cited

U.S. PATENT DOCUMENTS 9,371,313 B2 * 6/2016 Woolford ............. A61K 31/352

* cited by examiner

*Primary Examiner* — Russell G Fiebig
(74) *Attorney, Agent, or Firm* — David LeCroy

(57) ABSTRACT

Plant-based inhibitors of MMP-9 that also function as PPAR-γ agonists, and the use of such plant-based inhibitors/agonists in modulating metabolic disorders is disclosed. The plant-based inhibitor/agonist is at least an extract obtained from the leaf of the genus *Vaccinium*.

5 Claims, 12 Drawing Sheets

Procyanidin A1

Procyanidin A2

Procyanidin B1;EC (4β→8)-C
Procyanidin B2;EC (4β→8)-EC
Procyanidin B3;C-(4α→8)-C
Procyanidin B4;C-(4α→8)-EC Procyanidin B5;EC (4β→8)-EC
Procyanidin B6;C-(4α→8)-C
Procyanidin B7;BC (4β→8)-C
Procyanidin B8;C- (4α→8)-EC Quercetin Isoquercetin 6'-O-trans-Caffeoylarbutin Avicularin Procyanidin A1

Procyanidin A2

Procyanidin B1;EC (4β→8)-C
Procyanidin B2;EC (4β→8)-EC
Procyanidin B3;C (4α→8)-C
Procyanidin B4;C (4α→8)-EC Procyanidin B5;EC (4β→6)-EC
Procyanidin B6;C (4α→6)-C
Procyanidin B7;BC (4β→6)-C
Procyanidin B8;C (4α→6)-EC Monotropein, 6,7-Dihydro, 10-O-(4-hydroxy-e-cinnamayl)

Myricetin 3-arabinofuranoside

6'-O-trans-Caffeoylarbutin

Avircularin

1. Cyanidin-3-galactoside (R=Gal)
2. Cyanidin-3-arabinoside (R=Ara)

3. Peonidin-3-galactoside (R=Gal)
4. Peonidin-3-arabinoside (R=Ara)

5. Malvidin-3-galactoside (R=Gal)

BOTANICAL MODULATOR OF METABOLIC DISORDERS

CROSS REFERENCE TO RELATED APPLICATIONS

The present application is a divisional application of U.S. patent application Ser. No. 16/561,574, filed 5 Sep. 2019, which claims the benefit of U.S. Patent Application No. 62/728,119, filed 7 Sep. 2018, the disclosure of which is incorporated herein in its entirety by reference.

BACKGROUND OF THE INVENTION

Field of the Invention

The present invention generally relates to MMP-9 inhibitors and PPAR-γ agonists, and more particularly to plant-based or botanical inhibitors of MMP-9 that also function as PPAR-γ agonists, namely, cranberry (*Vaccinium macrocarpon*) leaves, and the use of such plant-based inhibitors/agonists in modulating one or more metabolic disorders.

Under normal circumstances, extracellular matrix ('ECM') synthesis and degradation is tightly regulated. While planned degradation of ECM is an important feature of tissue repair and remodeling, uncontrolled changes of the ECM are associated with many diseases such as inflammation, cancer, and cardiovascular dysfunction. Among the cardiovascular diseases, myocardial infarction ('MI') is one of the most highly prevalent heart conditions in the United States. It is linked to long term complication and high mortality rate as a result of progression of post myocardial infarction remodeling to congestive heart failure.

Matrix metalloproteinases ('MMPs') are among the key enzymes that play a crucial role in the remodeling of cardiac ECM. MMPs are a family of structurally related, zinc-dependent endopeptidases that degrade several components of the ECM, with their increased expression and/or activity associated with various pathophysiological processes. In particular, MMP-9 (also known as Gelatinase B) plays a major role in myocardial ECM remodeling. MMP-9 has consistently been found to increase in the early times post-MI, and its levels positively correlated with heart failure severity. Hence, reducing the expression level and/or activity of MMP-9 could have beneficial effects in cardiovascular health.

MMP-9 is also one of the enzymes involved in the degradation of articular cartilage matrix. Cartilage is the main component of articular structure and consists of chondrocytes that are embedded in a dense and highly organized ECM. ECM is synthesized by the chondrocytes and is composed of a collagenous network that primarily contains type II collagen, along with glycosaminoglycans ('GAGs') and associated proteoglycans. Collagen forms a fibrillar network and provides the cartilage matrix with tensile strength whereas aggrecan is the major cartilage proteoglycan, drawing water into the matrix and allowing it to resist compression. Along with aggrecan breakdown, degradation of collagen is a central feature of arthritis. Pro-inflammatory cytokines such as tumor necrosis factor alpha ('TNF-α'), interleukin 1 ('IL-1') and IL-6 are known to play important roles in cartilage matrix degradation in the articular cartilage through a cascade of events that lead to stimulation of aggrecanase and matrix metalloproteinase (such as MMP-9) production. A reduction in MMP-9 by a botanical extract would indicate the extract's ability to contribute to healthier joint structure through maintenance of intact cartilage.

MMP-9 seems to be involved in the enzymatic process of many pathological conditions. Cancer (breast, pancreas, lung, bladder, colorectal, ovarian, prostate and brain); periodontal disease (periodontitis and gingivitis); secondary complications of diabetes (plaque formation in atherosclerosis); delayed wound healing (venous leg ulcers); inflammatory bowel disease complications (Crohn's disease); neuroinflammation (multiple sclerosis); and gastric ulcer are a few of numerous human ailments affected by the presence of this enzyme. Therefore, modulating the expression and/or activity of MMP-9 is vital to correcting many chronic and acute diseases.

Insulin resistance and impaired glucose tolerance are two key imbalances in metabolic syndrome with strong association to abdominal obesity, hypertension, and dyslipidemia. People affected by these disorders have a greater risk of developing cardiovascular diseases, type II diabetes, chronic low-grade local tissue inflammation and increased susceptibility to other disease conditions such as fatty liver, sleep disturbances and cancer. Through the years, several anti-hyperglycemic products have been developed to combat these challenges by targeting ways to increase insulin secretion, sensitize tissues and organs for insulin, increase glucose uptake and transport, and decrease absorption of carbohydrates from the gut. Among these targets, for example, Peroxisome proliferator activated receptor gamma ('PPAR-γ') influences insulin sensitivity of peripheral tissues by controlling the expression of many factors secreted from adipose tissue, such as adiponectin, leptin, resistin and tumor necrosis factor-alpha (TNF-α). PPAR-γ can also directly upregulate glucose transporter type 4 (Glut4) and hence modulate glucose homeostasis.

PPARs are ligand-activated transcription factors that regulate target gene expression. Following endogenous or exogenous agonist binding, PPAR receptors heterodimerize with retinoid X receptor (RXR) and bind to PPAR response elements (PPREs) located in the promoter region of target genes resulting in regulation of gene expression. In addition to effects on maintenance of metabolic homeostasis, PPARs regulate the expression of genes involved in lipid metabolism, adipogenesis, and inflammation.

There are at least three PPAR subtypes (α, β and γ) with diverse tissue expression, suggesting that each of these subtypes may have specific functions. Among them, PPAR-γ is known to have two isoforms—PPAR-γ1 and PPAR-γ2. PPAR-γ1 is abundantly expressed in adipose tissue, large intestine, and hematopoietic cells, and to a lower extent in kidney, liver, muscles, pancreas, and small intestine. In contrast, PPAR-γ2 is limited to white and brown adipose tissues.

Activation of PPAR-γ is one of the key steps in the process of differentiation of pre-adipocyte precursor cells into adipocytes with an ultimate effect on the modulation of glucose metabolism. For instance, the potent exogenous agonists of PPAR-γ—the thiazolidinediones (a/k/a 'TZDs' or glitazones, e.g., troglitazone, rosiglitazone, and pioglitazone)—are known to improve insulin responsiveness, increase glucose uptake and lipid storage of adipocytes through this pathway, making them a good intervention choice for diabetes mellitus.

Phytomedicine plays an important role in the management of most of these diseases, with plants being a potential source of natural modulators of metabolic disorders. Consequently, there is a growing research interest in plants that contain modulators and health-promoting phytoconstituents as potential therapeutic agents. Medicinal plants provide a safe, cost-effective, ecological alternative to chemical modulators, which can be toxic on prolonged exposure.

Cranberry (*Vaccinium macrocarpon*) was introduced to European settlers by Native Americans, who used the berries for treating kidney stones and urinary tract health problems. Since then, cranberry has been used to treat a variety of ailments, including urinary tract infections, stomach ailments, scurvy, vomiting, and weight loss by a large portion of the North American population. There are a number of cranberry fruit extracts on the market, and cranberry fruit juice is a common and popular beverage alone or in combination with other juices. Further, there is excellent recognition by the public of the health benefits of cranberry fruit-based products.

A strong body of scientific research documents the contribution of the consumption of berries to the three targets of functional foods: (a) health maintenance; (b) reduced risk of obesity; and (c) reduced risk of chronic diet-related diseases (e.g., cardiovascular disease, type 2 diabetes, and metabolic syndrome). In addition to the fruits, the leaves of berry plants have been used in traditional remedies. Leaf extracts have often been used against several diseases, such as colds, urinary tract inflammation, diabetes, and ocular dysfunction by Native Americans and other populations.

Still, little is known about the composition of leaves of berry plants and their beneficial properties. It is known that the main bioactive compounds in berry leaves are similar to those found in their fruits (i.e., phenolic acids and esters, flavanols, anthocyanins, and procyanidins). It is also known that the concentrations of these compounds can vary from family to family within the genera *Vaccinium*.

As part of a healthy lifestyle and a well-balanced, wholesome diet, supplementation is recognized as an important means of modulating various metabolic disorders. As noted above, there is a need for effective, nontoxic, natural compounds with such modulating activity. The present invention provides one such solution.

BRIEF SUMMARY OF THE INVENTION

Disclosed herein is a composition comprising the botanical extract of the leaf of *Vaccinium macrocarpon*, wherein the botanical extract exhibits modulation of one or more metabolic disorders. The botanical extract can be present in an amount of about 1.0 µg/mL or greater. Preferably, the botanical extract is present in an amount of about 1.0 µg/mL to about 2000.0 µg/mL.

In one aspect, the composition exhibits MMP-9 inhibition. In such instances, the botanical extract is present in the composition in an amount of about 1.0 µg/mL to about 2000.0 µg/mL.

In a further aspect, the composition exhibits PPAR-γ agonist activity. In such instances, the botanical extract is present in the composition in an amount of about 50.0 µg/mL to about 2000.0 µg/mL.

Also disclosed herein is a dietary supplement having modulatory properties for one or more metabolic disorders. The supplement comprises the botanical extract of the leaf of *Vaccinium macrocarpon* in a therapeutically effective amount. The botanical extract of the leaf exhibits MMP-9 inhibition and/or PPAR-γ agonist activity. The botanical extract of the leaf of *Vaccinium macrocarpon* is present in the supplement in an amount of about 1.0 µg/mL or greater.

The present invention further provides a method of modulating one or more metabolic disorders in a subject by administering a composition comprising the botanical extract of the leaf of *Vaccinium macrocarpon* at a concentration of about 1.0 µg/mL to about 2000.0 µg/mL.

DETAILED DESCRIPTION OF THE INVENTION

Figure 1A:
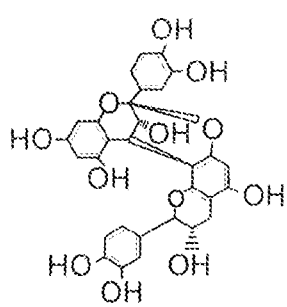
FIGS. 1A and 1B provides the chemical structures of various procyanidin and flavonoid compounds identified in cranberry fruit extract (E1) (non-exhaustive).
Figure 1A:
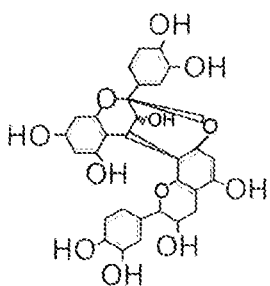
Figure 1A:
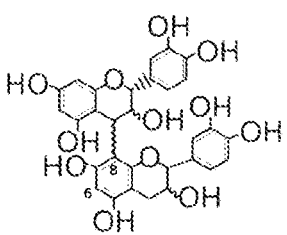
Figure 1A:
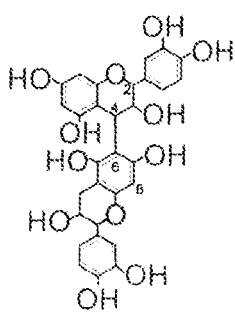
Figure 1A:
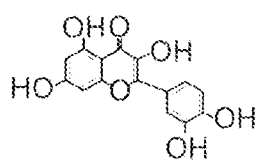
Figure 1A:
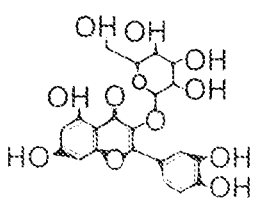
Figure 1A:
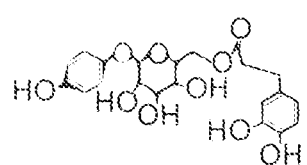
Figure 1A:
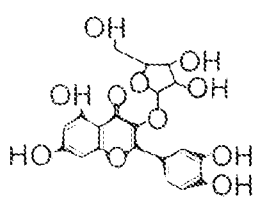
Figure 1B:
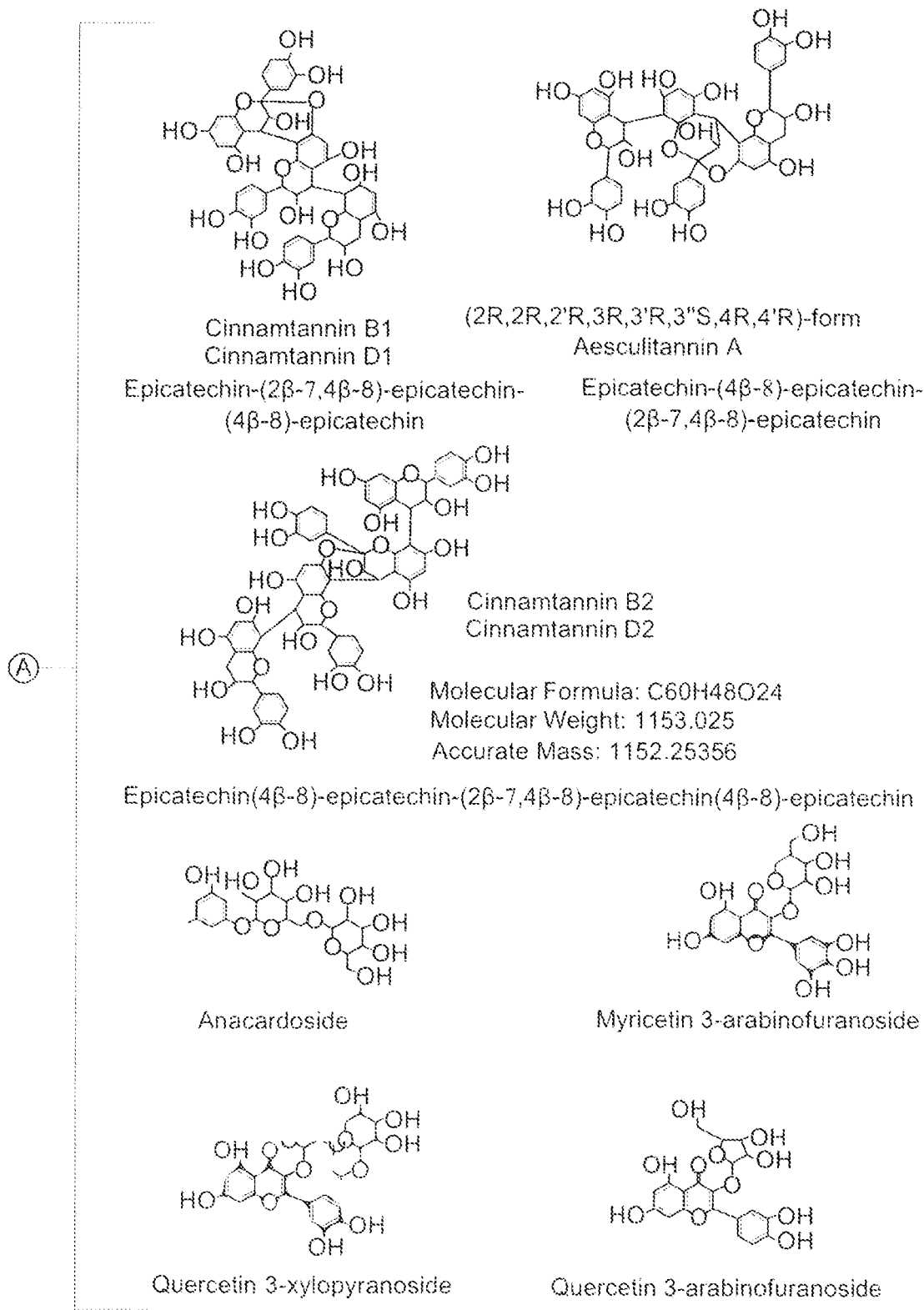
Figure 2A:
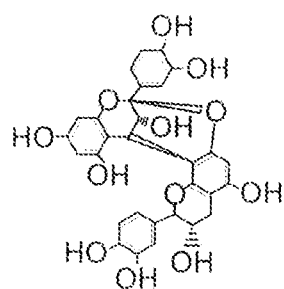
FIGS. 2A and 2B provides the chemical structures of various procyanidin and flavonoid compounds identified in cranberry leaf extract (E2) (non-exhaustive).
Figure 2A:
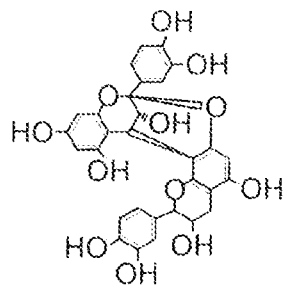
Figure 2A:
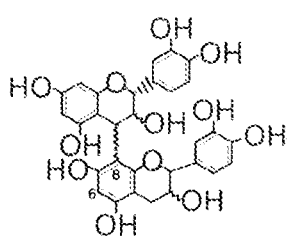
Figure 2A:
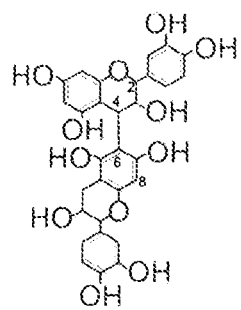
Figure 2A:
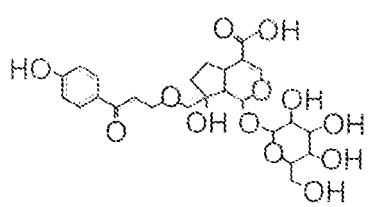
Figure 2A:
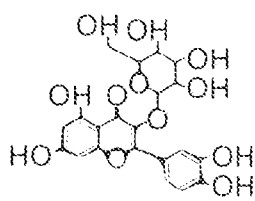
Figure 2A:
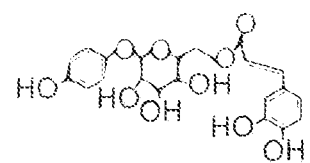
Figure 2A:
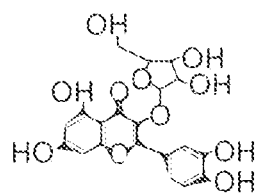
Figure 2B:
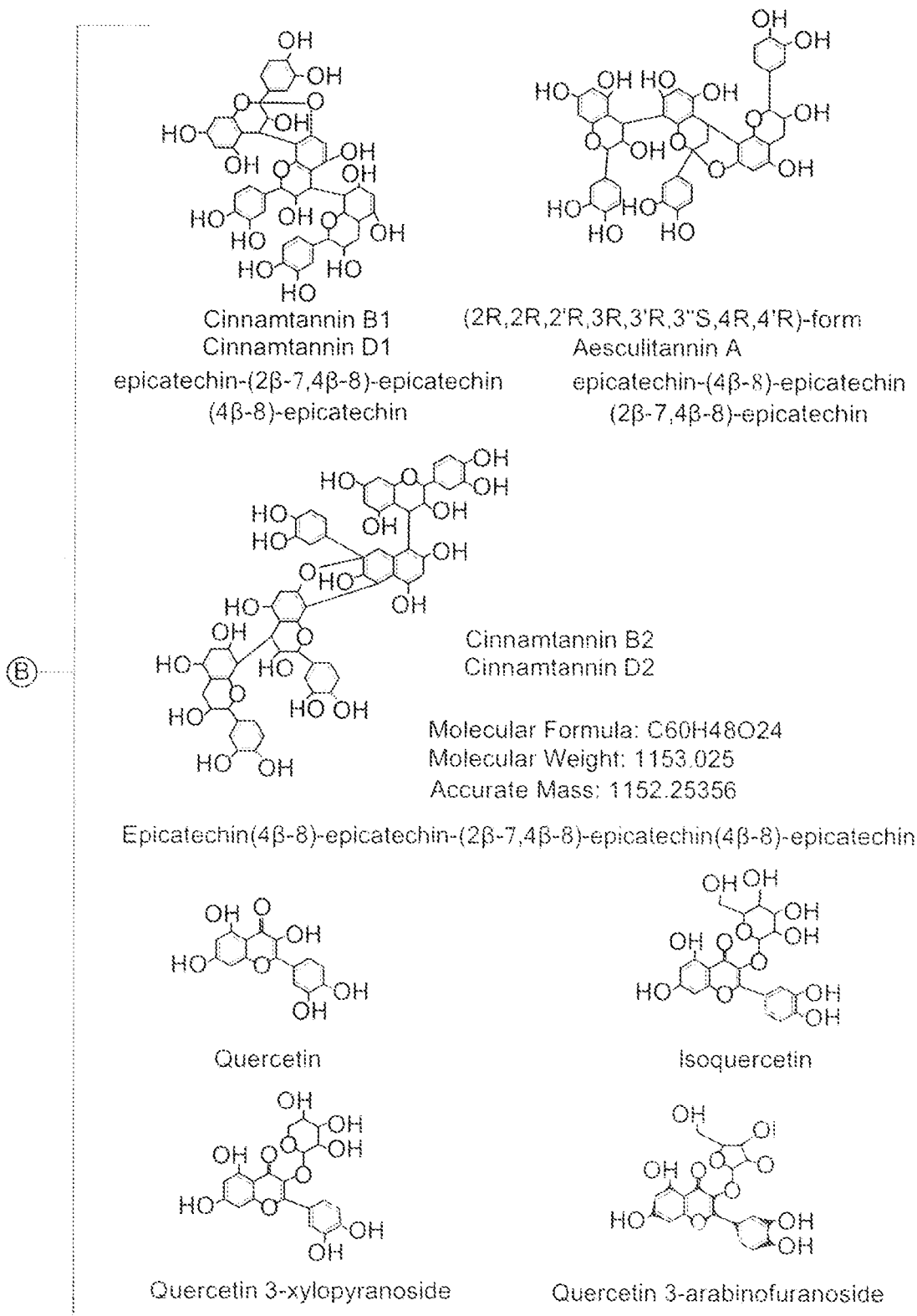

Disclosed herein is a botanical extract of the fruit and/or leaf of a plant comprising multiple procyanidins and bioflavonoids, wherein the fruit extract has been standardized to an anthocyanin content of about 1.90 mg/g, based on total weight of cyanidin-3-galactoside, cyaniding-3-arabinoside, peonidin-3-galactoside, peonidin-3-arabinoside, and malvidin-3-galactoside in the fruit extract, and wherein the botanical extract comprises at least an extract from the genus *Vaccinium*.

The present invention is further based on the surprising discovery that the leaf of the cranberry plant (*Vaccinium macrocarpon*) is substantially higher in certain flavonoids than the cranberry fruit. In particular, the extract from the leaves has a flavonoid content of at least 20 times greater than the flavonoid content of the fruit of the cranberry plant. In another embodiment, the extract from the leaves comprises a procyanidin trimers and procyanidin tetramers content of at least 23 times and 700 times greater than the procyanidin trimers and procyanidin tetramers content, respectively, of the fruit of the cranberry plant. Accordingly, in one embodiment, the botanical extract is from at least the leaves of *Vaccinium macrocarpon*. Further, the botanical extract from at least the leaves of *Vaccinium macrocarpon* may have applications in modulating one or more metabolic disorders.

When the botanical extract is at least the leaf of the plant, the botanical extract can be present in the composition in an amount of about 1.0 µg/mL or greater. For example, the leaf extract can be present in the composition in an amount of about 1.0 µg/mL to about 1000.0 µg/mL.

For the present application, the term "composition" refers to a product that treats, improves, promotes, increases, manages, controls, maintains, optimizes, modifies, reduces, inhibits, or prevents a particular condition associated with a natural state, biological process or disease or disorder. For example, a composition improves the inhibition of metastasis and/or reduces inflammation, and the like in a subject. The term composition includes, but is not limited to, pharmaceutical (i.e., drug), over-the counter (OTC), cosmetic, food, food ingredient or dietary supplement compositions that include an effective amount of an extract, at least one component thereof, or a mixture thereof. Exemplary compositions include cream, cosmetic lotion, pack or powder, or as an emulsion, lotion, liniment foam, tablets, plasters, granules, or ointment. Compositions can also include beverages, for example, beverages infused with an effective amount of an extract, or a tea satchel containing an effective amount of an extract. Non-limiting examples of food compositions containing an effective amount of an extract include baked goods, protein powders, meat products, dairy products, and confectionary.

As used herein, the term "extract" or "botanical extract" refers to a solid, viscid, or liquid substance or preparation that includes one or more active ingredients of a substance of at least the plant *Vaccinium* (e.g., *Vaccinium macrocarpon* and/or *Vaccinium oxycoccos*). Preferably, the active ingredient is derived from the extract of the leaf of the plant. The extract can be prepared using a solvent such as water, lower alcohols of 1 to 4 carbon atoms (e.g., methanol, ethanol, butanol, etc.), ethylene, acetone, hexane, ether, chloroform, ethylacetate, butylacetate, dichloromethane, N,N-dimethylformamide ('DMF'), dimethylsulfoxide ('DMSO'), 1,3-butylene glycol, propylene glycol, and combinations thereof, but also a fraction of the crude extract in such a solvent. So long as it assures the extraction and preservation of the active ingredient(s), any extraction method may be employed.

As used herein, the term "effective amount" or "therapeutically effective amount" of a pure compound, composition, extract, extract mixture, component of the extract, and/or active agent or ingredient, or a combination thereof refers to an amount effective at dosages and for periods of time sufficient to achieve a desired result. For example, the "effective amount" or "therapeutically effective amount" refers to that amount of a pure compound, composition, extract, botanical extract, extract mixture, botanical extract mixture, component of the extract, and/or active agent or ingredient, or a combination thereof of this invention which, when administered to a subject (e.g., mammal, such as a human), is sufficient to effect treatment, such as improving the inhibition of oxidation and/or reducing inflammation, and the like in a subject. The amount of a composition, extract, botanical extract, extract mixture, botanical extract mixture, component of the extract, and/or active agent or ingredient of this disclosure that constitutes an "effective amount" or "therapeutically effective treatment" will vary depending on the active agent or the compound, the condition being treated and its severity, the manner of administration, the duration of treatment, or the age of the subject to be treated, but can be determined routinely by one of ordinary skill in the art having regard to his own knowledge and to this disclosure.

The term "pharmaceutically acceptable" means those drugs, medicaments, extracts or inert ingredients, which are suitable for use in contact with the tissues of humans and lower animals without undue toxicity, incompatibility, instability, irritation, and the like, commensurate with a reasonable benefit/risk ratio.

The terms "administer", "administered", "administers", and "administering" are defined as providing a composition to a subject via a route known in the art, including but not limited to intravenous, intra-arterial, oral, parenteral, buccal, topical, transdermal, rectal, intramuscular, subcutaneous, intraosseous, transmucosal, or intraperitoneal routes of administration. In preferred embodiments, oral routes of administering a composition are suitable.

As used herein, the term "subject" or "individual" includes mammals to which a composition may be administered. Non-limiting examples of mammals include humans, non-human primates, canines, felines, equines, bovines, rodents (including transgenic and non-transgenic mice) or the like. In some embodiments, the subject is a non-human mammal, and in some embodiments, the subject is human.

As used herein, the term "carrier" refers to a composition that aids in maintaining one or more plant extracts in a soluble and homogeneous state in a form suitable for administration, which is nontoxic, and which does not interact with other components in a deleterious manner.

The term "modulation" or "modulator" as used herein generally refers to a substance that indirectly influences (or modulates) one or more metabolic disorders.

The term "metabolic disorder" as used herein refers to abnormal chemical reaction(s) that alter normal metabolic process(es). Non-limiting examples of metabolic disorders include glucose metabolism disorders, DNA repair-deficiency disorders, lipid metabolism disorders, malabsorption disorders, and calcium metabolism disorders. Symptoms of such disorders are often found in a cluster of conditions referred to as metabolic syndrome, including hypertension (increase blood pressure), abdominal obesity (excess body fat around the waist), and dyslipidemia (abnormal cholesterol or triglyceride levels), that occur together, increasing one's risk of heart disease, stroke, and diabetes.

Unless indicated otherwise, all proportions and percentages recited throughout this disclosure are by weight.

The present invention provides a plant-based extract capable of modulating one or more metabolic disorders. More particularly, the present invention is directed towards a botanical extract of the leaves of the cranberry plant from the genus *Vaccinium*. Such botanical extracts have been found to be capable of inhibiting MMP-9 and acting as an agonist for PPAR-γ, thereby limiting adverse enzyme activity in the case of MMP-9 inhibition, and/or promoting ligand binding when acting as an agonist for PPAR-γ. PPAR-γ influences insulin sensitivity of peripheral tissues by controlling the expression of many factors secreted from adipose tissue such as adiponectin, leptin, resistin and tumor necrosis factor-alpha (TNF-α). PPAR-γ can also directly upregulate glucose transporter type 4 (Glut4) and hence modulate glucose homeostasis. By limiting MMP-9 and/or promoting PPAR-γ activity, one or more metabolic disorders can be mitigated, for example, inflammation, metastasis, and/or insulin sensitivity. Further, by limiting MMP-9 and/or promoting PPAR-γ activity, one or more symptoms of metabolic syndrome may be mitigated, including hypertension, obesity, and/or dyslipidemia.

Useful botanical extracts capable of inhibiting MMP-9 and/or acting as an agonist for PPAR-γ according to the present invention include botanical extracts from the genus *Vaccinium*. More particularly, the botanical extract can be obtained from a plant chosen from *Vaccinium arctostaphy-*

*los, Vaccinium macrocarpon, Vaccinium oxycoccos, Vaccinium microcarpum, Vaccinium microcarpum, Vaccinium erythrocarpum, Vaccinium arboretum, Vaccinium crassifolium, Vaccinium angustifolium, Vaccinium boreale, Vaccinium caesariense, Vaccinium caespitosum, Vaccinium corymbosum, Vaccinium darrowii, Vaccinium deliciosum, Vaccinium elliotii, Vaccinium floribundum, Vaccinium hirsutum, Vaccinium membranaceum, Vaccinium myrsinites, Vaccinium myrtilloides, Vaccinium myrtillus, Vaccinium ovalifolium, Vaccinium ovatum, Vaccinium padifolium, Vaccinium pallidum, Vaccinium parvifolium, Vaccinium praestans, Vaccinium reticulatum, Vaccinium scoparium, Vaccinium stamineum, Vaccinium tenellum, Vaccinium uliginosum, Vaccinium virgatum,* and/or *Vaccinium vitisidaea.* Preferably, the botanical extract is at least from *Vaccinium macrocarpon, Vaccinium oxycoccos, Vaccinium microcarpum,* and/or *Vaccinium microcarpum.* More preferably, the botanical extract is at least from *Vaccinium macrocarpon*; even more preferably a botanical extract from the leaf of *Vaccinium macrocarpon.*

Compositions capable of inhibiting MMP-9 and/or acting as an agonist for PPAR-γ according to the present invention may include one or more compounds that may function as active ingredients and which are a component of the botanical extract. For example, the compound can be a phytochemical present in the plant from which the plant extract is obtained. The compound may be at least partially responsible for inhibiting MMP-9 and/or acting as an agonist for PPAR-γ. The compound can be any compound capable of inhibiting MMP-9 and/or acting as an agonist for PPAR-γ. In one embodiment, the compound is chosen from the phytochemicals isoquercetin, quercetin-3-glycoside, kaempferol glycoside, and/or procyanidins (e.g., A, B, trimer, tetramer).

Generally, one or more parts of a plant can be used to produce a botanical extract including, but not limited to, the root, the stem, the leaf, the flower, the fruit, the seed, and the testa of the seed. In the present invention, at least the leaf of the plant is used—alone or with other plant parts, particularly the fruit—to produce the plant extract. The fruit and leaf from the *Vaccinium* plant can be commercially obtained from various sources. The extract of the fruit and leaf can be obtained using any suitable extraction technique.

In this regard, one or more parts of the plant, particularly the leaf of the *Vaccinium* plant, can be collected and milled. Thereafter, the milled material can be extracted using a suitable solvent. The solvent can be removed in a concentration step. For example, the extracted material can be screened or filtered to create a supernatant and a cake. The cake can be pressed to remove a substantial portion of the liquid, which can be added to the supernatant. The cake can then be dehydrated and used as a fiber source. The supernatant can be distilled to remove the solvent or a portion thereof, to form a plant extract liquid concentrate. The removed solvent can be recycled. The concentrate can be dried (e.g., by spray drying) to provide a dried plant extract. This dried plant extract can be assayed and/or standardized as described herein. Preferably, the dried plant extract is derived from *Vaccinium macrocarpon*, particularly the leaf of the plant *Vaccinium macrocarpon.*

Suitable solvents for the extraction process include water, alcohol, or mixtures thereof. Exemplary alcoholic solvents include, but are not limited to, $C_1$-$C_7$ alcohols (e.g., methanol, ethanol, propanol, isopropanol, and butanol), hydroalcohols or mixtures of alcohol and water (e.g., hydroethanol), polyhydric alcohols (e.g., propylene glycol and butylene glycol), and fatty alcohols. Any of these alcoholic solvents can be used in the form of a mixture. In one embodiment, the plant extract is extracted using ethanol, water, or a combination thereof (e.g., a mixture of about 70% ethanol and about 30% water). In another embodiment, the plant extract is extracted using only water.

In one embodiment, the plant extract can be obtained using an organic solvent extraction technique. In another embodiment, solvent sequential fractionation can be used to obtain the plant extract. Total hydro-ethanolic extraction techniques can also be used to obtain the plant extract. Generally, this is referred to as a lump-sum extraction.

Total ethanol extraction can also be used. This technique uses ethanol as the solvent. This extraction technique can generate a plant extract having fat soluble and/or lipophilic compounds in addition to water soluble compounds.

Another example of an extraction technique that can be used to obtain the plant extract is supercritical fluid extraction ('SFE'). In this extraction procedure, the material to be extracted may not be exposed to any organic solvents. Rather, carbon dioxide can be used as the extraction solvent—with or without a modifier—in super-critical conditions (>31.3° C. and >73.8 bar). Those skilled in the art will appreciate that temperature and pressure conditions can be varied to obtain the best yield of extract. This technique can generate an extract of fat soluble and/or lipophilic compounds, similar to a total hexane and ethyl acetate extraction technique.

The botanical extract generated in the process can include a broad variety of phytochemicals present in the extracted material. The phytochemicals can be fat soluble or water soluble. Following collection of the extract solution, the solvent can be evaporated, resulting in the extract.

The botanical extract can be standardized to a specified amount of a particular compound. For example, the botanical extract can be standardized to a specified amount of an active ingredient or phytochemical present in the extract.

The amount of plant extract present in the MMP-9 inhibitor and/or PPAR-γ agonist composition can depend upon several factors, including the desired level of MMP-9 inhibition and/or PPAR-γ increase in activity, the MMP-9 inhibition and/or PPAR-γ increase in activity level of a particular plant extract or component thereof, and other factors. Preferably, the plant extract is present in an amount of from about 0.005 wt % or greater, for example, from about 0.005 wt % to about 99.00 wt %, based on total weight of the composition.

The MMP-9 inhibitor and/or PPAR-γ agonist composition can include one or more acceptable carriers. The carrier can aid in enabling incorporation of the plant extract into an MMP-9 inhibitor and/or PPAR-γ agonist composition having a suitable form for administration to a subject. A wide number of acceptable carriers are known in the art, and the carrier can be any suitable carrier. The carrier is preferable suitable for administration to animals, including humans, and can be able to act as a carrier without substantially affecting the desired activity of the plant extract and/or any active ingredient. The carrier can be chosen based upon the desired administration route and dosage form of the composition.

Suitable dosage forms include liquid and solid forms. In one embodiment, the composition is in the form of a gel, a syrup, a slurry, or a suspension. In another embodiment, the composition is in a liquid dosage form such as a drink shot or a liquid concentrate. In a further embodiment, the composition is present in a solid dosage form, such as a tablet, a pill, a capsule, a dragée, or a powder. When in liquid or solid dosage form, the composition can be in a food delivery form suitable for incorporation into food for delivery.

Examples of suitable carriers for use in solid forms (particularly tablet and capsule forms) include, but are not limited to, organic and inorganic inert carrier materials such as gelatin, starch, magnesium stearate, talc, gums, silicon dioxide, stearic acid, cellulose, and the like. The carrier can be substantially inert.

As an example, silicified microcrystalline cellulose can be used as a carrier or binder. Silicified microcrystalline cellulose is a physical mixture of microcrystalline cellulose and colloidal silicon dioxide. One such suitable form of silicified microcrystalline cellulose is ProSolv SMCC® 90, available from Penwest Pharmaceutical Co., Patterson, N.J. Silicon dioxide, in addition to that provided by the silicified microcrystalline cellulose, may be added to the composition as a processing aid. For example, silicon dioxide can be included as a glidant to improve the flow of powder during compression in the manufacturing of solid dosage units, such as tablet.

In another embodiment, the carrier is at least a functional carrier such as buckwheat or spelt. By the addition of functional carriers into the composition, additional benefits may be provided such as lower glycemic index compared to standard carriers such as those mentioned above. Further, functional carriers can be allergen free (e.g., buckwheat), and by adding them into the production process, the botanical extracts of the invention may benefit from the flavonoids of these functional carriers, such as rutin and quercetin. Also, the high fiber content of these functional carriers may facilitate and regulate intestinal transit. Finally, the added mineral benefit of selenium found in spelt may aid in metabolism.

The MMP-9 inhibitor and/or PPAR-γ agonist composition can include other inert ingredients, such as lubricants and/or glidants. Lubricants aid in the handling of tablets during manufacturing, such as during ejection from dies. Glidants improve powder flow during tablet compression. Stearic acid is an example of an acceptable lubricant/glidant.

The MMP-9 inhibitor and/or PPAR-γ agonist composition can be made in solid dosage form, such as tablets and capsules. This form provides a product that can be easily transported by an individual to a place of eating, such as a restaurant, and taken prior to, during, or after consumption of a foodstuff. The composition can be formulated into dosage units containing suitable amounts of the plant extract and/or active ingredient that permit an individual to determine an appropriate number of units to take based upon appropriate parameters, such as body weight, foodstuff size, or carbohydrate (e.g., sugar) content.

In one embodiment, the botanical extract is present in the composition in a therapeutically effective amount, such as an amount of about 1.0 μg/mL or greater, preferably from about 1.0 μg/mL to about 1000.0 μg/mL, more preferably from about 15.0 μg/mL to about 750.0 μg/mL. The composition can be administered as a single dose, or in multiple doses. In one example, the compound is administered in up to three doses per day. For example, the compound may be administered prior to a meal, during a meal, or after a meal. In one embodiment, the composition is a dietary supplement having MMP-9 inhibitor and/or PPAR-γ agonist properties containing cranberry leaf extract in a therapeutically effective amount.

The dosage can be chosen to provide a level of inhibitory effect in a single unit that may be effective for some individuals and/or some foodstuffs, while also allowing for relatively simple dosage increases to provide other levels of inhibitory effects that can be effective for other individuals and/or other foodstuffs.

The inhibiting composition can be in a form adapted for oral ingestion. This form can be configured as a single dosage form intended to provide a specified dose of the plant extract. For example, the single dosage form can be a powder, a pill, a tablet, a capsule, or a drink shot. The single dosage form can include, for example, from about 1.0 μg/mL to about 2000.0 μg/mL of the plant extract.

EXAMPLES

Examples—Materials and Chemical Profiling

Example 1—Preparation of 70% Ethanol Extracts from Cranberry Fruit and Cranberry Leaf Dried cranberry fruit powder (*Vaccinium macrocarpon*) (60 g) was loaded into three 100 ml stainless steel tubes and extracted twice using a solvent of 70% ethanol in DI water with a Thermo Scientific™ Dionex™ ASE 350 Accelerated Solvent Extractor at a temperature of 80° C. and pressure of 1500 psi. The extract solution was automatically filtered and collected. The combined ethanol extract solution was evaporated with a rotary evaporator under vacuum to give a crude 70% ethanol fruit extract ('E1').

Dried ground cranberry leaf powder (*Vaccinium macrocarpon*) (140 g) was loaded into seven 100 ml stainless steel tubes and extracted twice using a solvent of 70% ethanol in DI water with a Thermo Scientific™ Dionex™ ASE 350 Accelerated Solvent Extractor at a temperature of 80° C. and pressure of 1500 psi. The extract solution was automatically filtered and collected. The combined ethanol extract solution was evaporated with a rotary evaporator under vacuum to give a crude 70% ethanol leaf extract ('E2').

The extraction results are provided in the following Table 1—

TABLE 1

Extraction of Cranberry fruit and Cranberry leaf

| Plant Part | Extract ID | Plant Powder (g) | Extract Weight (g) | Extraction Yield (wt %) |
|---|---|---|---|---|
| Fruit | E1 | 60 | 27.40 | 45.67% |
| Leaf | E2 | 140 | 23.75 | 16.96% |

Example 2—Chemistry Profiling of Cranberry Fruit and Cranberry Leaf Extracts

Flavonoid compounds present in the cranberry fruit extract E1 and cranberry leaf extract E2 were determined using ultra high-pressure liquid chromatography ('HPLC') and mass spectrometry (ACQUITY® UPLC I-Class and XEVO® GS-XT-QT of system, both available from Water Corporation, Milford, Massachusetts USA). The column used was an ACQUITY® UPLC HSS T3 2.1×100 mm, 1.8 μm, with a column temperature of 40° C. and a sample temperature of 15° C. For the mobile phase, Solvent A was 10% acetonitrile ('ACN') in water (0.1% Formic Acid), and Solvent B was ACN. The acquisition range was 100-1500 Daltons ('Da'), and the acquisition mode was electrospray ionization ('ESI') (−). Table 2 below provides the HPLC conditions—

TABLE 2

HPLC condition for analyzing E1 and E2 extracts

| Extract | Run Time (min) | Injection Volume (μL) | Concentration |
|---|---|---|---|
| E1 | 20.00 | 1.00 | 5 mg/mL |
| E2 | 20.00 | 2.00 | 1 mg/mL |

Peak identification was based on accurate mass only. Multiple isomers may have been identified as the same compound due to the limitation of the database. For example, eight (8) procyanidin B1-B8 compounds having the same molecular weight of 578.528 were not differentiated in this analysis.

Procyanidins and flavonoid glycosides such as quercetin, isoquercetin, and myricetin 3-arabinofuranoside were detected and identified based on accurate mass in E1 at relatively low content. Chemical structures of compounds detected in E1 (non-exhaustive) are illustrated in FIG. 1. The following table lists compounds identified in E1 based on accurate mass—

TABLE 3

Compounds Identified in E1

| Compound Name | Neutral Mass (Da) | Observed Neutral Mass (Da) | Observed m/z | Mass error (ppm) | Observed RT (min) | Detector counts |
|---|---|---|---|---|---|---|
| Vaccihein A | 378.09508 | 378.0935 | 377.0862 | −4.3 | 0.65 | 22406 |
| Procyanidin B | 578.14243 | 578.1445 | 577.1373 | 3.6 | 0.66 | 13886 |
| 8-[5-(3,4-Dihydroxy-7-hydroxy-4-oxo-2H-1-benzopyran-2-yl)-2-hydroxyphenyl]-2,3-dihydro-7-hydroxy-2-(4-hydroxypheny)-4H-1-benzopyran-4-one | 510.13147 | 510.1291 | 509.1218 | −4.7 | 0.68 | 21507 |
| Procyanidin trimer | 864.19016 | 864.1939 | 863.1867 | 4.4 | 0.72 | 19512 |
| Monotropein | 390.11621 | 390.1165 | 389.1092 | 0.8 | 0.93 | 7503 |
| Orcinol gentiobioside, Anacardioside | 448.15808 | 448.1574 | 447.1501 | −1.6 | 3.20 | 22920 |
| 2-O-Benzoylglucose; D-form | 284.08960 | 284.0894 | 283.0822 | −0.6 | 3.54 | 18514 |
| Leptosin | 462.11621 | 462.1164 | 461.1091 | 0.4 | 3.59 | 51758 |
| Leptosin | 462.11621 | 462.1164 | 461.1091 | 0.4 | 3.63 | 38344 |
| 2-O-Benzoylglucose; D-form | 284.08960 | 284.0893 | 283.0820 | −1.0 | 3.71 | 6747 |
| Procyanidin trimer | 864.19016 | 864.1872 | 863.1800 | −3.4 | 3.79 | 5716 |
| Dunalianoside B | 450.11621 | 450.1150 | 449.1077 | −2.7 | 3.95 | 7628 |
| Dunalianoside B | 450.11621 | 450.1147 | 449.1074 | −3.5 | 4.12 | 7014 |
| Procyanidin trimer | 864.19016 | 864.1862 | 863.1789 | −4.6 | 4.15 | 45918 |
| 2-O-Benzoylglucose; D-form | 284.08960 | 284.0891 | 283.0819 | −1.6 | 4.17 | 6085 |
| Procyanidin tetramer | 1152.25355 | 1152.2530 | 1151.2457 | −0.5 | 4.37 | 5523 |
| Procyanidin trimer | 864.19016 | 864.1866 | 863.1793 | −4.1 | 4.98 | 5966 |
| Myricetin 3-arabinofuranoside | 450.07983 | 450.0793 | 449.0721 | −1.1 | 5.17 | 8296 |
| Myricetin 3-arabinofuranoside | 450.07983 | 450.0795 | 449.0723 | −0.6 | 5.51 | 16797 |
| Myricetin 3-arabinofuranoside | 450.07983 | 450.0803 | 449.0730 | 1.0 | 5.64 | 46613 |
| Vaccinoside | 536.15299 | 536.1530 | 535.1457 | 0.0 | 5.78 | 28664 |
| Vaccinoside | 536.15299 | 536.1533 | 535.1460 | 0.6 | 5.97 | 72372 |
| Procyanidin A | 576.12678 | 576.1274 | 575.1201 | 1.1 | 6.13 | 119550 |
| Monotropein; 6,7-Dihydro, 10-O-(4-hydroxy-E-cinnamoyl) | 538.16864 | 538.1692 | 537.1620 | 1.1 | 6.16 | 57726 |
| Monotropein; 6,7-Dihydro, 10-O-(4-hydroxy-E-cinnamoyl) | 538.16864 | 538.1699 | 537.1626 | 2.4 | 6.33 | 151522 |
| Vaccinoside | 536.15299 | 536.1536 | 535.1463 | 1.1 | 6.35 | 7992 |
| Avicularin | 434.08491 | 434.0858 | 433.0785 | 2.0 | 6.38 | 62923 |
| Vaccinoside | 536.15299 | 536.1534 | 535.1461 | 0.7 | 6.46 | 5222 |
| Avicularin | 434.08491 | 434.0860 | 433.0787 | 2.5 | 6.56 | 52683 |
| Avicularin | 434.08491 | 434.0859 | 433.0787 | 2.4 | 6.79 | 130113 |
| Myricetin 3′-methyl ether | 332.05322 | 332.0536 | 331.0463 | 1.1 | 9.83 | 10303 |
| 4-O-Acetyl-6-trans-caffeoylarbutin | 476.13186 | 476.1319 | 475.1247 | 0.1 | 12.14 | 12950 |

Abundant bioflavonoids were identified in E2, including avicularin, isoquercetin, kaempferol, glycosides, and others. Chemical structures of compounds detected in E2 (non-exhaustive) are illustrated in FIG. 2. The following table lists compounds identified in E2 based on accurate mass—

TABLE 4

Compounds Identified in E2

| Compound Name | Neutral Mass (Da) | Observed Neutral Mass (Da) | Observed m/z | Mass error (ppm) | Observed RT (min) | Detector counts |
|---|---|---|---|---|---|---|
| Procyanidin B | 578.14243 | 578.1441 | 577.1368 | 2.8 | 0.67 | 13416 |
| Monotropein | 390.11621 | 390.1155 | 389.1082 | −1.8 | 0.72 | 31923 |
| Procyanidin trimer | 864.19016 | 864.1872 | 863.1799 | −3.4 | 0.75 | 9024 |

TABLE 4-continued

Compounds Identified in E2

| Compound Name | Neutral Mass (Da) | Observed Neutral Mass (Da) | Observed m/z | Mass error (ppm) | Observed RT (min) | Detector counts |
|---|---|---|---|---|---|---|
| Procyanidin tetramer | 1152.25355 | 1152.2512 | 1151.2439 | −2.0 | 0.75 | 33165 |
| Myricetin 3-arabinofuranoside | 450.07983 | 450.0792 | 449.0720 | −1.3 | 0.94 | 6589 |
| Monotropein | 390.11621 | 390.1166 | 389.1093 | 0.9 | 0.94 | 43918 |
| Procyanidin tetramer | 1152.25355 | 1152.2502 | 1151.2429 | −2.9 | 2.36 | 28086 |
| Procyanidin B | 578.14243 | 578.1411 | 577.1338 | −2.3 | 3.19 | 10152 |
| Orcinol gentiobioside, Anacardioside | 448.15808 | 448.1582 | 447.1510 | 0.3 | 3.19 | 480731 |
| Procyanidin trimer | 864.19016 | 864.1878 | 863.1806 | −2.7 | 3.25 | 104158 |
| Procyanidin tetramer | 1152.25355 | 1152.2502 | 1151.2429 | −2.9 | 3.28 | 34709 |
| Procyanidin A | 576.12678 | 576.1260 | 575.1188 | −1.3 | 3.29 | 6558 |
| Procyanidin B | 578.14243 | 578.1418 | 577.1345 | −1.2 | 3.35 | 31488 |
| Orcinol gentiobioside | 448.15808 | 448.1581 | 447.1508 | 0.1 | 3.41 | 55958 |
| Procyanidin tetramer | 1152.25355 | 1152.2493 | 1151.2420 | −3.7 | 3.60 | 22964 |
| Orcinol gentiobioside, Anacardioside | 448.15808 | 448.1574 | 447.1501 | −1.5 | 3.63 | 9322 |
| Procyanidin trimer | 864.19016 | 864.1872 | 863.1799 | −3.5 | 3.80 | 53828 |
| Dunalianoside B | 450.11621 | 450.1157 | 449.1084 | −1.2 | 3.94 | 20828 |
| Procyanidin trimer | 864.19016 | 864.1883 | 863.1811 | −2.1 | 4.16 | 262966 |
| Procyanidin tetramer | 1152.25355 | 1152.2507 | 1151.2434 | −2.5 | 4.38 | 89683 |
| Procyanidin A | 576.12678 | 576.1261 | 575.1188 | −1.2 | 4.38 | 13405 |
| Procyanidin trimer | 864.19016 | 864.1870 | 863.1797 | −3.6 | 4.54 | 9939 |
| Procyanidin trimer | 864.19016 | 864.1885 | 863.1812 | −2.0 | 4.98 | 98041 |
| Procyanidin A | 576.12678 | 576.1262 | 575.1190 | −0.9 | 4.99 | 9959 |
| Procyanidin A | 576.12678 | 576.1257 | 575.1185 | −1.8 | 5.10 | 22194 |
| Procyanidin tetramer | 1152.25355 | 1152.2495 | 1151.2423 | −3.5 | 5.14 | 21067 |
| Procyanidin tetramer | 1152.25355 | 1152.2490 | 1151.2417 | −4.0 | 5.26 | 14044 |
| Procyanidin A | 576.12678 | 576.1264 | 575.1191 | −0.7 | 5.26 | 7671 |
| Procyanidin trimer | 864.19016 | 864.1871 | 863.1798 | −3.6 | 5.34 | 9598 |
| Procyanidin A | 576.12678 | 576.1246 | 575.1173 | −3.8 | 5.47 | 6853 |
| Procyanidin tetramer | 1152.25355 | 1152.2491 | 1151.2419 | −3.8 | 5.47 | 17471 |
| Procyanidin trimer | 864.19016 | 864.1873 | 863.1800 | −3.3 | 5.53 | 11401 |
| Myricetin 3-arabinofuranoside | 450.07983 | 450.0804 | 449.0732 | 1.4 | 5.63 | 22203 |
| Vaccinoside | 536.15299 | 536.1531 | 535.1458 | 0.1 | 5.78 | 98913 |
| Dunalianoside B | 450.11621 | 450.1164 | 449.1091 | 0.4 | 5.83 | 5653 |
| Vaccinoside | 536.15299 | 536.1531 | 535.1459 | 0.3 | 5.97 | 153237 |
| Procyanidin A | 576.12678 | 576.1275 | 575.1202 | 1.3 | 6.12 | 398543 |
| Procyanidin tetramer | 1152.25355 | 1152.2502 | 1151.2429 | −2.9 | 6.12 | 35819 |
| Jeediflavanone | 558.11621 | 558.1170 | 557.1097 | 1.4 | 6.12 | 5855 |
| Monotropein; 6,7-Dihydro, 10-O-(4-hydroxy-E-cinnamoyl) | 538.16864 | 538.1696 | 537.1623 | 1.7 | 6.15 | 208791 |
| Procyanidin trimer | 864.19016 | 864.1890 | 863.1817 | −1.4 | 6.20 | 65398 |
| Monotropein; 6,7-Dihydro, 10-O-(4-hydroxy-E-cinnamoyl) | 538.16864 | 538.1693 | 537.1620 | 1.2 | 6.33 | 353675 |
| Vaccinoside | 536.15299 | 536.1530 | 535.1457 | 0.0 | 6.35 | 6705 |
| Avicularin | 434.08491 | 434.0857 | 433.0785 | 1.9 | 6.38 | 512642 |
| Vaccinoside | 536.15299 | 536.1545 | 535.1472 | 2.8 | 6.47 | 9321 |
| Procyanidin A | 576.12678 | 576.1265 | 575.1192 | −0.5 | 6.47 | 11610 |
| Procyanidin tetramer | 1152.25355 | 1152.2511 | 1151.2438 | −2.1 | 6.47 | 33495 |
| Procyanidin trimer | 864.19016 | 864.1892 | 863.1819 | −1.1 | 6.48 | 113767 |
| Avicularin | 434.08491 | 434.0859 | 433.0787 | 2.4 | 6.56 | 916754 |
| 4-Hydroxyphenyl-gentioside | 434.14243 | 434.1441 | 433.1368 | 3.8 | 6.56 | 7559 |
| 3',4,4''',5',7,7''-Hexahydroxy-8,3'''-biflavanone | 542.12130 | 542.1229 | 541.1156 | 3.0 | 6.59 | 7805 |
| 3,5-Bis(3,4-dihydroxycinnamoyl)quinic acid | 516.12678 | 516.1259 | 515.1186 | −1.7 | 6.61 | 6367 |
| Avicularin | 434.08491 | 434.0859 | 433.0786 | 2.2 | 6.78 | 1907961 |
| 2,4,6-Trihydroxyphenylacetic acid; 2-O-(3,4-Dihydroxybenzoyl) | 320.05322 | 320.0541 | 319.0468 | 2.6 | 7.08 | 8233 |
| Dunalianoside B | 450.11621 | 450.1165 | 449.1092 | 0.6 | 7.42 | 19468 |
| Procyanidin A | 576.12678 | 576.1246 | 575.1173 | −3.9 | 7.49 | 6252 |
| Lyonside | 552.22068 | 552.2212 | 551.2139 | 0.9 | 7.50 | 42922 |
| Quercetin 3-glycosides; Monosaccharides, 3-O-[3-Hydroxy-3-methylglutaroyl-(4)-Î±L-rhamnopyranoside] | 592.14282 | 592.1432 | 591.1359 | 0.7 | 7.73 | 15267 |
| Leptosin | 462.11621 | 462.1171 | 461.1098 | 1.9 | 8.39 | 5097 |
| 8-[5-(3,4-Dihydroxy-7-hydroxy-4-oxo-2H-1-benzopyran-2-yl]-2-hydroxyphenyl]-2,3-dihydro-7-hydroxy-2-(4-hydroxyphenyl)-4H-1-benzopyran-4-one | 510.13147 | 510.1324 | 509.1251 | 1.8 | 8.63 | 8411 |
| Lyoniside | 552.22068 | 552.2210 | 551.2138 | 0.6 | 8.73 | 6492 |
| Procyanidin A | 576.12678 | 576.1270 | 575.1197 | 0.4 | 8.86 | 8440 |
| Procyanidin B | 578.14243 | 578.1420 | 577.1347 | −0.8 | 12.84 | 7997 |

Multiple procyanidins were found in E2 at substantially higher content compared to E1. Procyanidin dimers—including both A and B types—were found to be about fifty (50) times higher in E2 compared to E1 based on detector counts with mass-to-charge ratio ('m/z') at 575.11 and 577.13. Procyanidin trimers with observed m/z at 863.18 were present at about twenty-three (23) times higher in E2 compared to E1, whereas procyanidin tetramer with m/z at 1152.24 was over seven hundred (700) times higher in E2 compared to E1.

Similar bioflavonoids were also identified in E2 with much higher abundance, including isoquercetin, quercetin-3-arabinofuranoside, kaempferol glycoside, etc. based on LCMS analysis. Flavonoids with observed m/z at 463.093—identified with molecular formula $C_{21}H_{22}O_{10}$—are twenty (20) times higher for peak with retention time ('RT') at 6.38 min, and thirty-six (36) times higher for peak with RT at 6.78 min for E2 compared to corresponding peaks detected in E1. Overall detector counts of flavonoids in E2 are over twenty (20) times higher than flavonoids in E1 based on LCMS analysis.

Figure 3:
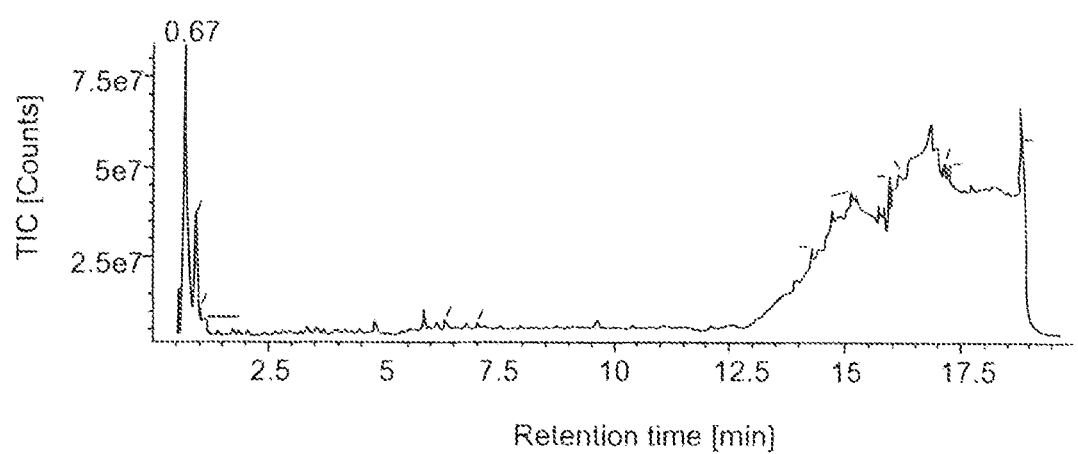
FIG. 3 is an LC/MS TIC chromatogram of cranberry fruit extract (E1).
Figure 4:
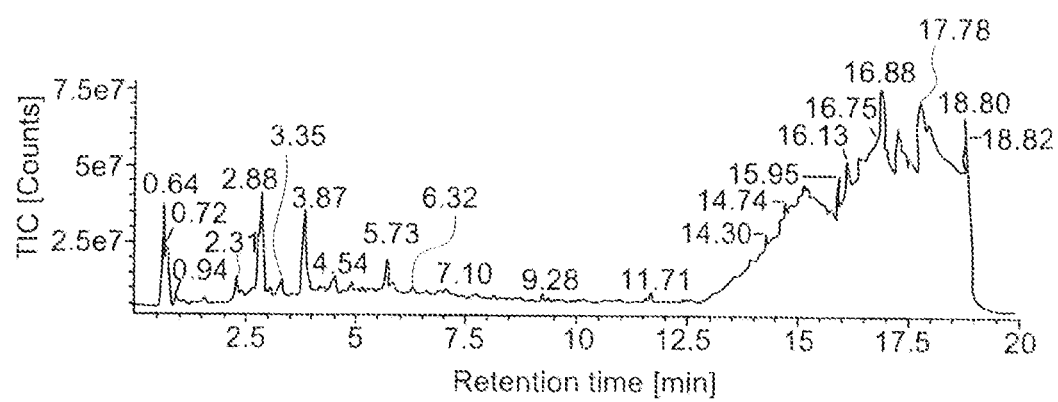
FIG. 4 is an LC/MS TIC chromatogram of cranberry leaf extract (E2).
Figure 5:
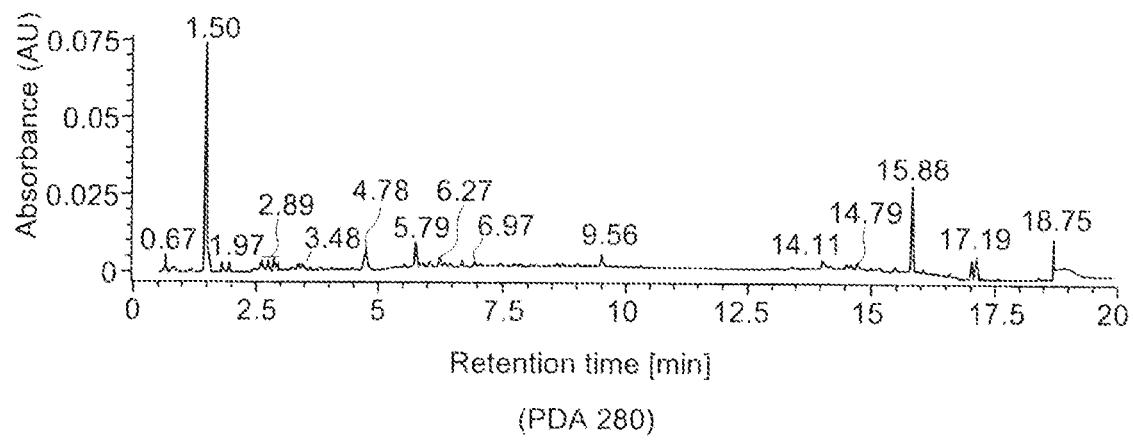
FIG. 5 is LC/PDA (wavelengths of 280 and 350 nm) chromatograms of cranberry fruit extract (E1).
Figure 5:
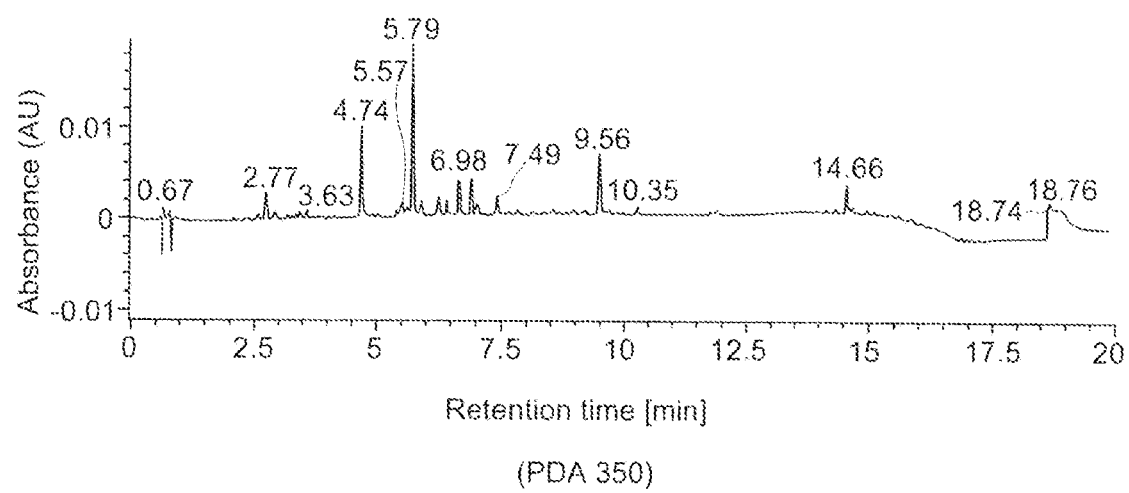

LCMS TIC, PDA 280 nm, and PDA 350 nm chromatograms are provided in FIG. 3 for E1 and FIG. 4 for E2. LCMS TIC chromatograms comparison between E2 and E1—illustrated in FIG. 5—clearly showed the higher contents for procyanidins and bioflavonoids in E2, while higher organic acid content was seen in E1 (FIG. 3).

Example 3—Anthocyanins Quantification

Anthocyanins quantification method was adapted from published HPLC analytical method (J. AGRIC. FOOD CHEM., "Separation, identification, quantification, and method validation of anthocyanins in botanical supplement raw materials by HPLC and HPLC-MS", Vol. 49(8), pp. 3515-3521 (2001)). HPLC system used was an Hitachi D7000 HPLC system, with a Phenomenex Luna 10 μm C18 column having a column size of 4.6×250 mm. Solvents used in the mobile phase were 0.5% phosphoric acid in $H_2O$ (Solvent A) and $H_2O/ACN/Acetic$ $Acid/H_3PO_4$ (50%:48.5%:1.0%:0.5%) (Solvent B). UV wavelength was 480 nm.

Reference standard cyanidin-3-glucoside was purchased from ChromaDex (Chicago, Illinois US). Cyanidin-3glucoside was prepared at 1 mg/mL concentration in 2% (v/v) HCl in methanol solution in 5 mL volumetric flask. The stock solution was further diluted by 1/5, 1/10, 1/20, and 1/100 times in 2% (v/v) HCl in methanol to give cyanidin-3-glucoside solutions at five concentrations of 1.00, 0.20, 0.10, 0.05 and 0.01 mg/mL, respectively. The five solutions were unitized to generate a calibration curve. Each sample was injected at 10 μL in three replicates. The calibration curve was determined based on the integrated peak areas. The correlation coefficient (R2) value of cyanidin-3-glucoside was determined at 0.9985.

Figure 7:
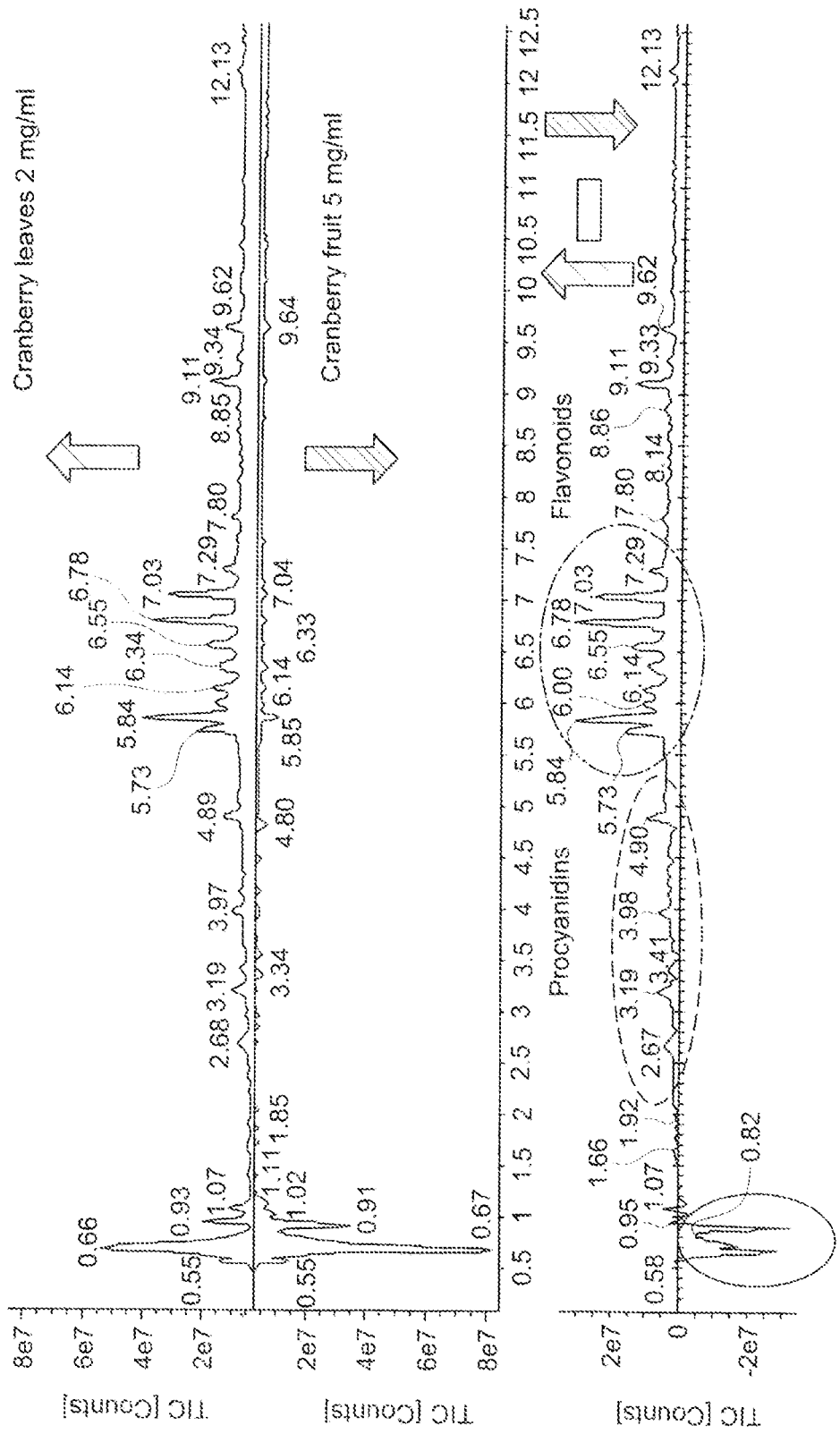
FIG. 7 is LC/MS TIC chromatograms comparison between cranberry fruit extract (E1) and cranberry leaf extract (E2).
Figure 8:
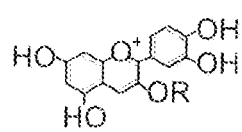
FIG. 8 provides the chemical structures of five anthocyanins identified in cranberry fruit extract (E1) present in the extract in an amount of 1.90 mg/g total anthocyanins.
Figure 8:
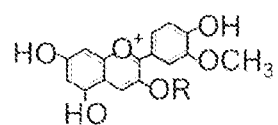
Figure 8:
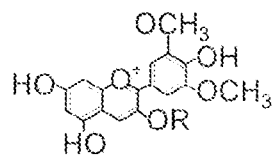
Figure 9:
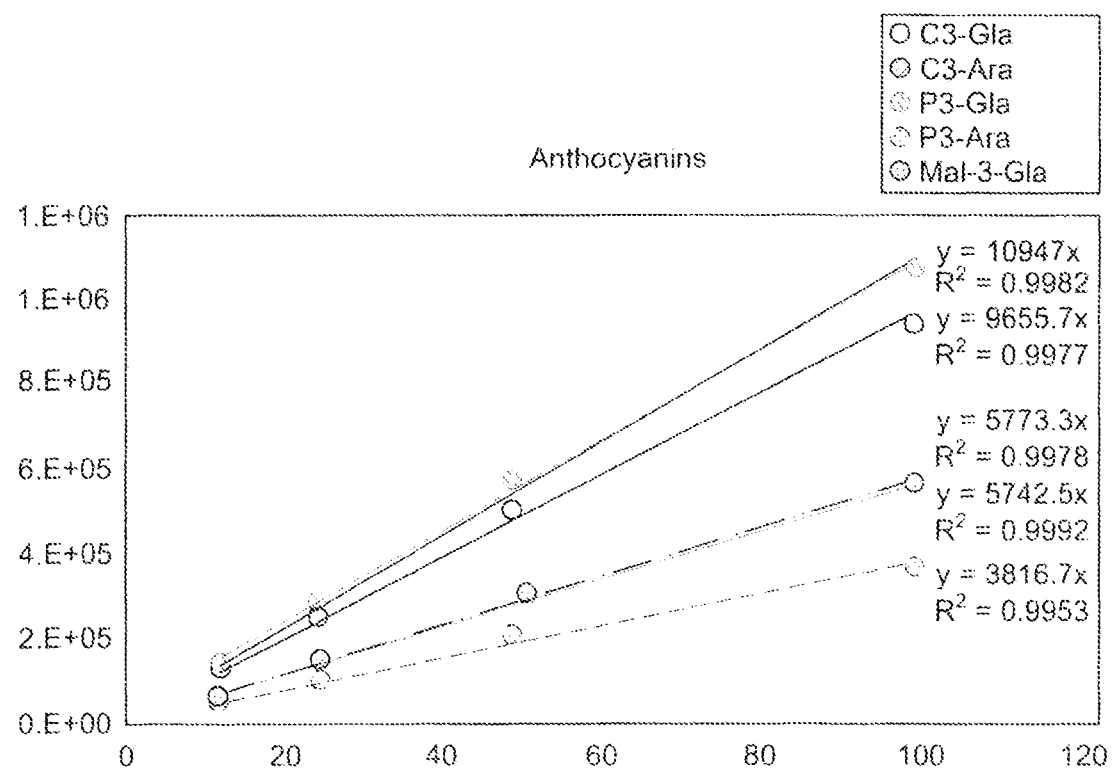
FIG. 9 is an illustration of the calibration curves of anthocyanins in cranberry fruit extract (E1).

Samples were prepared for analysis as follows. 12.5, 25.0, 50.0, and 100.0 mg of E1 were weighed. 1 mL of 2% (v/v) HCl in methanol was added to each sample, and then each sample was mixed by sonication for fifteen (15) minutes and vortexed at 10,000 rpm for five (5) minutes. 20 μL of supernatant of each solution was injected to HPLC in three replicates. Quantitative analysis of five (5) anthocyanin compounds at different concentrations demonstrated linearity with correlation coefficients $R^2$ from 0.9953 to 0.9982 (FIG. 7). The amount of each individual anthocyanin was calculated based on the integrated peak areas against cyaniding-3-glucoside at 0.05 mg/mL for the samples at a concentration of 25 mg/mL and 50 mg/mL, respectively.

Figure 6:
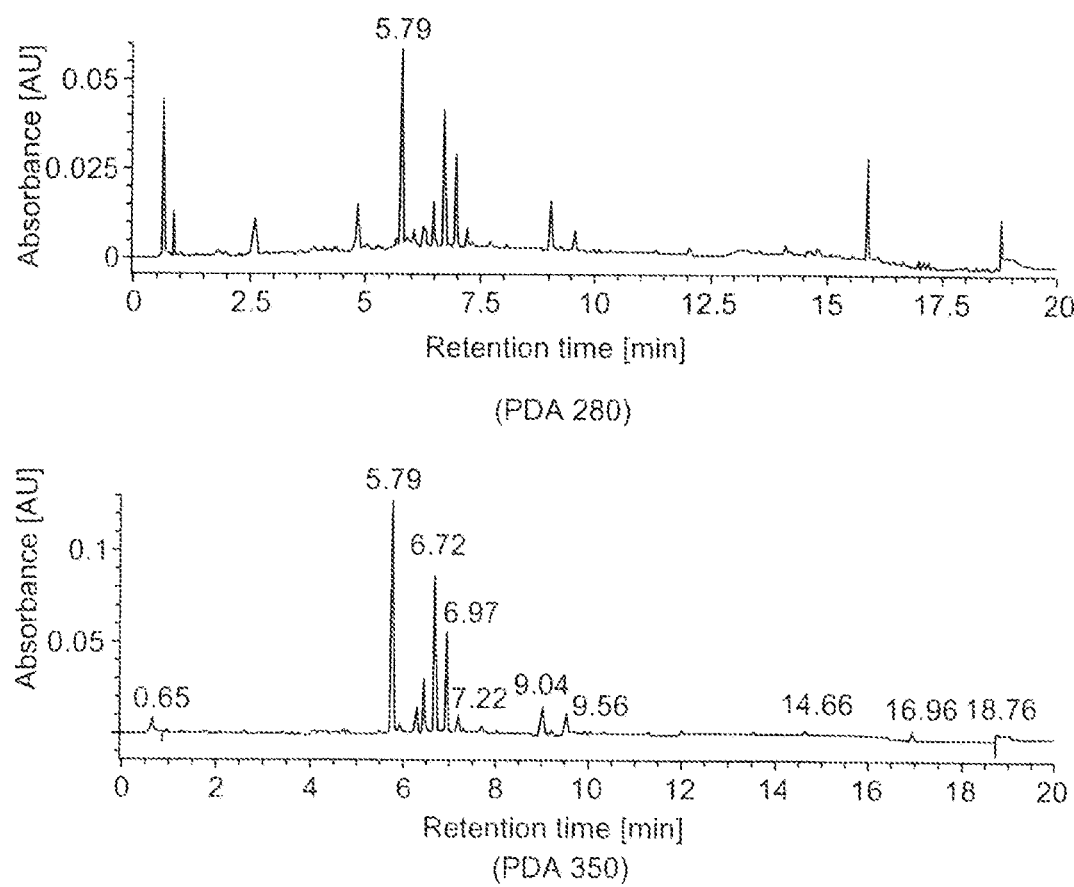
FIG. 6 is LC/PDA (wavelengths of 280 and 350 nm) chromatograms of cranberry leaf extract (E2).

Five anthocyanins were quantified in E1 with a total content of 1.903 mg/g as of dry weight of E1. These anthocyanins included Cyanidin-3-galactoside ('C3Gla'), Cyanidin-3-arabinoside ('C3-Ara'), Peonidin-3-galactoside ('P3-Gla'), Peonidin-3-arabinoside ('P3-Ara'), and Malvidin-3-galactoside ('Mal3-Gla'), based on analysis and comparison with those disclosed in the analytical method article and the article J. AOAC INT., "Determination of anthocyanins in Cranberry fruit and Cranberry fruit products by High-Performance Liquid Chromatography with Ultraviolet Detection; Single-Laboratory Validation", Vol. 94(2); pp. 459-466 (2011). These compounds are illustrated in FIG. 6. No anthocyanins were detected in E2.

TABLE 5

Amount of five anthocyanins calculated in E1

| mg/g | R1-25 mg/mL | R1-50 mg/mL |
|---|---|---|
| C3-Gla | 0.506 | 0.503 |
| C3-Ara | 0.276 | 0.275 |
| P3-Gla | 0.591 | 0.587 |
| P3-Ara | 0.200 | 0.195 |
| Mal-3-Gla | 0.330 | 0.331 |

Examples—Bioassay

Extracts of cranberry fruit (E1) and cranberry leaf (E2) were prepared with food-grade ethanol, and then filtered and dried as described above. Research grade reagents were used for the rest of the assay preparations. Extracts were dissolved in dimethyl sulfoxide ('DMSO') to a final concentration of 50 mg/mL, and then diluted in appropriate buffer for each bioassay to working concentrations.

Example 4—MMP-9 Inhibition

The MMP-9 Inhibitor Screening Assay Kit (Colorimetric) from abcam (Cambridge, United Kingdom; product no. ab139448) was utilized for the assay. E1 and E2 were diluted in assay buffer to test for MMP-9 inhibition in a dose curve and added to the wells of a 96-well half-volume microplate. NNGH—a broad spectrum MMP inhibitor—was used as a positive control at 1.3 μM. The MMP-9 enzyme was diluted 1:60 in assay buffer and added to the test wells and positive and negative controls at a final concentration of 0.9 units per well. The plate was incubated at 37° C. for 30 minutes to allow the inhibitors to bind the enzyme. MMP-9 substrate was diluted 1:25 in assay buffer and added to the wells at a final concentration of 100 μM. The plate was then continuously read for absorbance at 405 nm with readings every minute for 20 minutes. The slope over the linear range (first 10 minutes) was calculated for every well and percent inhibition of the test compounds and positive control were determined using the negative (untreated) control wells as the 100% mark.

Figure 10:
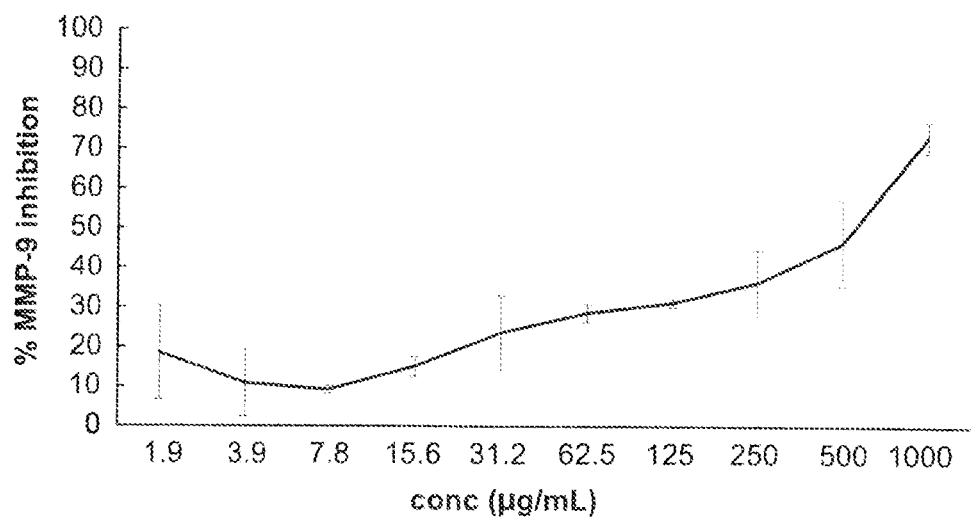
FIG. 10 is a graph illustrating cranberry leaf extract MMP-9 inhibition at 10 different concentrations.

Referring to FIG. 10, various degrees of MMP-9 inhibition were observed, depending on the concentration of Cranberry leaf extract. No Cranberry fruit extract inhibition was observed. Cranberry leaf extract MMP-9 inhibition was observed to be from about 1 μg/mL or greater, more particularly from about 1 μg/mL to at least about 1000 μg/mL, even more particularly from about 15 μg/mL to about 750 μg/mL, with an $IC_{50}$ of 579 μg/mL.

Example 5—PPAR-γ Activation

The PPAR-γ Ligand Screening/Characterization Assay Kit from BioVision (product #: K437-100) was used to test cranberry fruit (E1) and cranberry leaf (E2) extract for its ability to bind and activate PPAR-γ. This assay kit relies on the displacement of a fluorescent probe bound to the PPAR-γ protein by test samples. When test samples displace the fluorescent probe and bind to PPAR-γ, there is an observable decrease in fluorescent intensity. PPAR-γ Assay Probe was diluted 1:100 in DMSO. A master mix of PPAR-γ Protein, PPAR-γ Assay Probe, PPAR-γ Assay Buffer, and DMSO (10% final concentration) was prepared and added to test samples in a 384-well black plate for a total of 25 µL per well. The plate was incubated at room temperature for 5 minutes before being read on a fluorescent plate reader at the following wavelengths: excitation—405 nm, emission—460 nm. The samples were also read in the absence of PPAR-γ Assay Probe or PPAR-γ protein, and these blank values were subtracted from the experimental values to correct for interference. Percent inhibition was calculated as the difference in fluorescence intensity between the untreated control—which had 100% binding of fluorescent probe to PPAR-γ protein—and test samples divided by the value of the untreated control and expressed as a percent.

Figure 11:
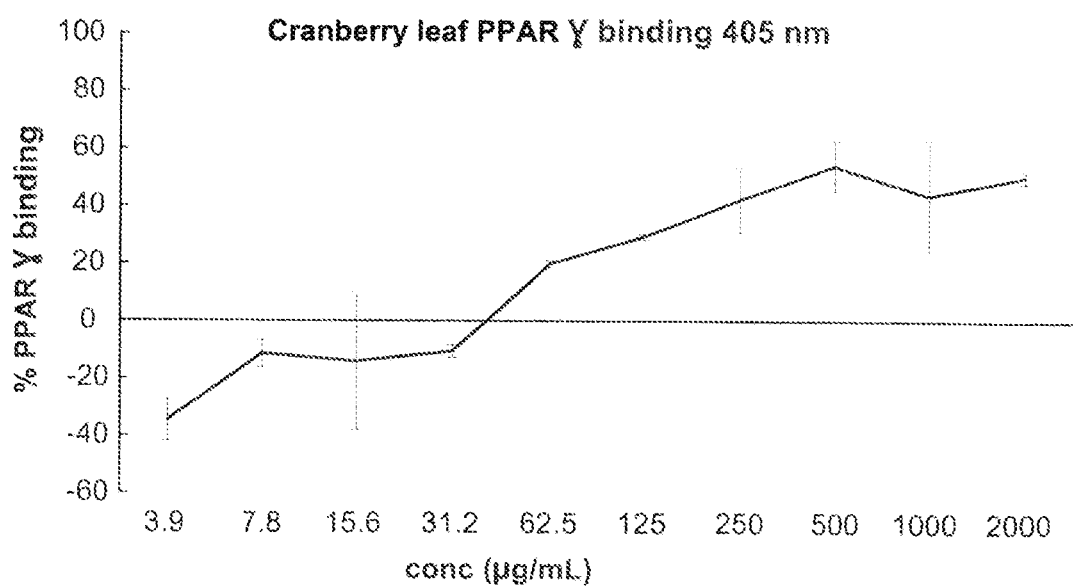
FIG. 11 is a graph illustrating cranberry leaf extract PPAR-γ ligand binding at 10 different concentrations.

Referring to FIG. 11, various degrees of intensity in PPAR-gamma ligand binding activities were observed for E2. E2 was tested at 10 different concentrations (3.9, 7.8, 15.6, 31.2, 62.5, 125, 250, 500, 1000, and 2000 µg/mL). E2 activation was observed to be from about 50.0 µg/mL to at least about 2000 µg/mL, more particularly from about 100 µg/mL to about 1000 µg/mL, even more particularly from about 125 µg/mL to about 500 µg/mL. An $IC_{50}$ of 384 µg/mL was observed for E2. No observable binding activity was noticed for E1.

The above data illustrates that the botanical extract of the leaf of *Vaccinium macrocarpon* has one or more compounds that may have some contributions in addressing the imbalance between the normal physiological condition and uncontrolled enzymatic expression/activity at the time of tissue remodeling or repair, that is, the extract exhibits modulation of one or more metabolic disorders.

The above description discloses several methods and materials of the present invention. This invention is susceptible to modifications in the methods and materials, as well as alterations in the fabrication methods and equipment. Such modifications will become apparent to those skilled in the art from a consideration of this disclosure or practice of the invention disclosed herein. Further, unless defined otherwise, all technical and scientific terms used herein have the same meaning as commonly understood to one of ordinary skill in the art to which this invention belongs. Consequently, it is not intended that this invention be limited to the specific embodiments disclosed herein, but that it covers all modifications and alternatives coming within the true scope and spirit of the invention as embodied in the attached claims.

We claim:

1. A composition comprising:
a botanical extract of a leaf of *Vaccinium macrocarpon*,
wherein the botanical extract is present in an amount of about 15.0 µg/mL to about 750.0 µg/mL,
wherein the botanical extract comprises at least isoquercetin and kaempferol and is free of anthocyanins,
wherein the extract is obtained by extracting dried ground cranberry leaf powder with a solvent of ethanol in water and evaporating the solvent, and
a carrier,
wherein the composition exhibits modulation of one or more metabolic disorders.

2. The composition according to claim 1, wherein the composition exhibits MMP-9 inhibition.

3. The composition according to claim 1, wherein the composition exhibits PPAR-γ agonist activity.

4. The composition according to claim 1, wherein the composition is a dietary supplement.

5. The dietary supplement according to claim 4, wherein the dietary supplement is in solid dosage form.

* * * * *